United States Patent
Serov et al.

(10) Patent No.: US 7,496,395 B2
(45) Date of Patent: Feb. 24, 2009

(54) LASER DOPPLER PERFUSION IMAGING WITH A PLURALITY OF BEAMS

(75) Inventors: Alexander Nikolaevich Serov, Lausanne (CH); Wiendelt Steenbergen, Enschede (NL); Frits Frans Maria De Mul, Almelo (NL)

(73) Assignee: Perimed AB (SE)

( * ) Notice: Subject to any disclaimer, the term of this patent is extended or adjusted under 35 U.S.C. 154(b) by 365 days.

(21) Appl. No.: 10/502,900

(22) PCT Filed: Feb. 3, 2003

(86) PCT No.: PCT/NL03/00074

§ 371 (c)(1),
(2), (4) Date: Apr. 7, 2005

(87) PCT Pub. No.: WO03/063677

PCT Pub. Date: Aug. 7, 2003

(65) Prior Publication Data

US 2005/0187477 A1      Aug. 25, 2005

(30) Foreign Application Priority Data

Feb. 1, 2002   (EP)   .................................. 02075406

(51) Int. Cl.
*A61B 5/05* (2006.01)
(52) U.S. Cl. .................. 600/407; 600/473; 600/476
(58) Field of Classification Search .................. 600/404, 600/473–477, 407, 310, 504; 235/454; 348/223.1; 356/39, 337, 345, 341, 319–320; 250/356.1
See application file for complete search history.

(56) References Cited

U.S. PATENT DOCUMENTS

| 6,045,511 | A | 4/2000 | Ott et al. |
| 6,055,322 | A | 4/2000 | Hanna et al. |
| 6,263,227 | B1 * | 7/2001 | Boggett et al. .............. 600/407 |
| 2001/0012408 | A1 | 8/2001 | Misek et al. |
| 2002/0050518 | A1 * | 5/2002 | Roustaei ..................... 235/454 |
| 2002/0191085 | A1 * | 12/2002 | Jaspers .................... 348/223.1 |

OTHER PUBLICATIONS

Biers, J.D. et al. "Quasi real-time digital version of single-exposure speckle photography for full-field monitoring of velocity or flow fields" Optics Communications, North-Holland Publishing Co., Amsterdam, NL, vol. 116, No. 1, Apr. 15, 1995 XP004013250; ISSN: 0030-4018, p. 38, right-hand column, paragraph 2, p. 40, right hand column.
International Search Report dated Apr. 25, 2003.

* cited by examiner

*Primary Examiner*—Eric F Winakur
*Assistant Examiner*—Lawrence N Laryea
(74) *Attorney, Agent, or Firm*—Greenberg Traurig, LLP

(57) ABSTRACT

Laser Doppler Perfusion Imaging system including a laser light source (2), an image detector (4), and signal detector (6); the laser light source (2), in use, being arranged for illuminating a selected area of interest (12) on a sample (10) for determining perfusion related data of the sample (10), the image detector, in use, being arranged for capturing an image of the sample (10), and the signal detector (6), in use, being arranged for detecting a laser Doppler signal from the selected area of interest (12) on the sample (10), wherein the laser light source (2) comprises optical means (3) for creating a laser beam comprising a plurality of beams.

15 Claims, 7 Drawing Sheets

Imaged frame, 192x192 pixels

*Fig 5b*

*Fig 5d*
Before occlusion

*Fig 5c*

*Fig 5e*
During occlusion

LASER DOPPLER PERFUSION IMAGING WITH A PLURALITY OF BEAMS

FIELD OF THE INVENTION

The present invention relates to a Laser Doppler perfusion Imaging system as defined in the preamble of claim 1. Furthermore, the present invention relates to a method to be carried out in such a system as defined in the preamble of claim 12.

PRIOR ART

Laser Doppler Perfusion Imaging (LDPI) is a relatively new non-invasive non-contact optical technique to measure the blood flow in skin and other human tissues. With this technique visualisation of blood flow over a large tissue area is possible. The outcome of the method is a 2-D map of blood perfusion defined as the average blood cell velocity multiplied by the blood cell concentration in the measuring volume.

When tissue is illuminated by laser light, some of the photons are scattered by moving blood cells and undergoes a slight frequency shift due to the Doppler effect. The mixing of the Doppler shifted and zero-Doppler-shifted (unshifted) photons on the remote photodetector causes intensity fluctuations with Doppler frequencies. The spectrum of these fluctuations yields information about concentration and mean velocity of moving red blood cells.

There are many situations in routine clinical medicine where 2-D Images of the blood flow over a certain area of tissue are important or very desirable, e.g. burns and plastic surgery, wound healing, dermatology, diabetology, rheumatology, neurology, oncology, pharmacology, vascular and transport surgery. In such cases laser Doppler image sensors are used.

Various techniques for blood flow imaging were suggested. Two different LDPI systems have been described by Wårdell et al. in "Laser Doppler perfusion imaging by dynamic light scattering", IEEE Trans. on Biomed. Eng. 40 (4), 309-316 (1993) and by Essex and Byrne in "A laser Doppler scanner for imaging blood flow in skin", J. Biomed. Eng. 13, 189-193 (1991). They illuminate the tissue by a narrow collimated laser beam and use a detector at 20-100 cm distance from the tissue to observe the light remitted from the illuminated area. By scanning the beam over a certain tissue area, a 2-D perfusion image is obtained. A difference between the two systems is the presence of lenses in the detection system by Essex and Byrne, whereas the LDPI system described by Wårdell et al. does not incorporate focusing of scattered light. In both systems the scanning takes an appreciable time since the scanning speed is limited by the trade-off between laser Doppler signal lower cut-off frequency and image quality. Also, a substantial rise in the noise level at low frequencies appears when using a continuously moving beam as used by Essex et al.

Patent application WO 9743950 by Boggett and Huang discloses an apparatus for imaging microvascular blood flow that enables a method of laser Doppler measurements based on an array of independent photodetectors. Further, Boggett and Huang disclose that the probing laser beam can be shaped by a beam shaper to obtain circular cross section diverging beam which has a approximately uniform power distribution over one more than half the beam width. Such illumination is required to obtain a required signal to noise ratio. Also, shaping the beam into a line-shaped beam is possible. The line-shaped beam may scan across an area in a step mode.

Fujii et al. describe in Appl. Opt. 26, "Evaluation of blood flow by laser speckle image sensing. Part 1", 5321-5325 (1987) a real-time technique for observation of blood flow over an area of the body using a linear CCD (Charge Coupled Device) array to monitor at one instant a line of tissue, and a scanning mirror to extend this line to a two-dimensional area. Later, Fujii applied this technique for mapping retinal blood flow using a 2-D CCD array without scanning mirror as described in "Real-time visualization of retinal microcirculation by laser flowgraphy", Opt. Eng. 34, 753-757 (1995). However, the speed of the system was not enough to resolve fast changes in the Doppler signal. This is caused by the integration of the signal variation during the scanning time interval in the sensor, which has an averaging effect on the resulting overall signal.

Briers suggested in "Capillary blood flow monitoring using laser speckle contrast analysis (LASCA)", J. Biomed. Opt. 4, 164-175 (1999), an alternative full-field real-time technique, called LASCA (Laser Speckle Contrast Analysis), which is based on the time-varying speckle phenomena closely related to laser Doppler as published by J. D. Briers in "Laser Doppler and time-varying speckle: a reconciliation", J. Opt. Soc. Am. A 13, 345-350 (1996): The LASCA technique was successfully used in clinic by Dunn et al., as published in "Dynamic imaging of cerebral blood flow using laser speckle", J. of Cerebral Blood Flow and Metabolism 21, 195-201 (2001). Dunn et al. used a 2-D array CCD camera with focusing optics to detect the speckle pattern formed by light remitted from the tissue illuminated by a divergent laser beam.

Analysis of the speckle pattern contrast gives information about the conception and average velocity of red blood cells. The main disadvantage of LASCA compared with the other techniques is the loss of resolution caused by the need to avenge over a block of pixels in order to produce the spatial statistics used in the analysis.

Main drawbacks of present laser Doppler imagers are:

Use of moving parts (mirrors for laser beam steering, or scanning) causes disturbance of the signal. Mechanical vibration of the scanning mirror deteriorates the measurement accuracy.

Scanning beam 2-D flow imaging takes long time: the time or space resolution of the system is poor.

Present full-frame laser imagers have also either poor time or poor spatial resolution limited by the dynamic range of the detector by Konishi et al or by the imaging approach of Briers et al., respectively, Superimposing the mapped flow onto a digital photograph of the examined area is often difficult since flow-detecting part (photodiode) and observation part (CCD) of the imagers are separated.

Dependence of the signal response on the tissue surface reflectivity affects correct interpretation of measurements on heterogeneous tissue surface: if tissue has a high reflectivity contrast, saturation or under-sensitivity of the photo-detector causes distortion of the flow map.

A simple way to improve the flow map frame rate of a Laser Doppler Perfusion Imaging system is to use a parallel detection scheme. This approach allows one to avoid movement of the laser beam used in standard laser Doppler imagers and, hence, to speed-up measurements, CCD cameras have already been used as detection devices for this purpose. However, for laser Doppler applications, this kind of detector suffers from two major disadvantages. The integration time is too high compared with the modulation period of the interferometric signal. Moreover, the dynamic range of the CCD camera is strongly limited by the DC light level inherent in the signal that reaches the detector. This limitation makes CCD cameras unsuitable for laser Doppler imaging.

SUMMARY OF THE INVENTION

It is an object of the present invention to improve prior art Laser Doppler Perfusion Imaging systems.

To obtain this object, the present invention relates to a Laser Doppler Perfusion Imaging system as described above characterised in that the laser light source comprises optical means for creating a laser beam comprising a plurality of beams.

The optical means (diffractive or adaptive) is capable of creating a laser beam comprising a plurality of beams arranged in some pattern. Such a pattern may comprise a (dot) matrix form, a rectangular array of beams, or any other conceivable pattern of beams, etc.

By using a beam profile comprising a plurality of beams arranged in a pattern, advantageously the Laser Doppler Perfusion Imaging system according to the present invention allows an increase of intensity in the beams, which increases the signal-to-noise-ratio during measurements. Thus, accuracy of detecting a signal is improved. Further, the application of increased intensity by using a plurality of beam profiles allows depth-resolved Laser Doppler Perfusion Imaging measurements.

Moreover, the present invention relates to a Laser Doppler Perfusion Imaging system comprising a laser light source, an image detector, and signal detector; the laser light source, in use, being arranged for illuminating a selected area of interest on a sample for determining perfusion-related data of said sample, the image detector, in use, being arranged for capturing an image of the sample, and the signal detector, in use, being arranged for detecting a laser Doppler signal from the selected area of interest on the sample, characterised in that the image detector embodies the signal detector, the image detector being a two-dimensional random access high pixel readout rate image sensor.

Advantageously, in a Laser Doppler Perfusion Imaging system according to the present invention digital photography and Doppler signal measurement are performed by a single detector. Mapping of perfusion data on the actual measured object is greatly simplified, in particular for medical applications.

For example, such a two-dimensional random access high pixel readout rate image sensor may be a CMOS imager.

Further, due to the characteristics of two-dimensional random access high pixel readout rate image sensors, in a Laser Doppler Perfusion Imaging system according to the present invention faster and more reliable measurements and analysis are possible than in Laser Doppler Perfusion Imaging systems of the prior art.

Advantageously, depth-resolved measurements are feasible when using the Laser Doppler Perfusion Imaging system according to the present invention. The detector elements of the CMOS image sensor measure a laser Doppler signal as a function of the lateral distance of an incoming laser beam focussed on the sample. At larger lateral distance between detector element position and the image of the incoming laser beam (source), the detected photons have a larger average penetration depth than those photons detected at a distance closer to the source.

Both these and other advantages will be explained in more detail with reference to the drawings and the description of preferred embodiments.

Furthermore, the present invention relates to a method to be carried out in such a system as defined in claim 12 of the accompanying claims.

BRIEF DESCRIPTION OF DRAWINGS

Below, the invention will be explained with reference to some drawings, which are intended for illustration purposes only and not to limit the scope of protection as defined in the accompanying claims.

DESCRIPTION OF PREFERRED EMBODIMENTS

As an alternative for detectors applied in prior art Laser Doppler Perfusion Imaging systems, in the present invention a two-dimensional random access high pixel readout rate image sensor such as a CMOS image sensor is used. Those skilled in the art will recognise that any type of MOS-based sensor may be used as detector as well.

CMOS (Complementary Metal Oxide Semiconductor) image sensors progressively developed over the last few years. CMOS image sensor devices are in some way very similar to CCDs. Both technologies are based on photosensitive diodes or gates in silicon. In both solid state devices photons are converted into an electrical charge. The main difference between CMOS and CCD image sensors is basically, that a CMOS image sensor is a 2-D matrix of photo-diodes, which can be addressed randomly at a high sampling rate (as described by B. Dierickx et al., in "Random addressable active pixel image sensors", Proc. SPIE 2950, 2-7 (1996)), while in CCD sensors the sampling rate of one pixel is limited to the frame rate. Therefore, CMOS image sensors are able to make both a photographic image of the object under interest and detect rapid intensity changes at each point of the object. Another essential difference is the integration time inherent to CCD but not to all CMOS image sensors. In CMOS image sensors, the photo-current is continuously converted into output voltage as opposed to CCD in which the current is accumulating during a certain period of time that limits the dynamical range of the system, as encountered by Fujii et al.

Figure 1:
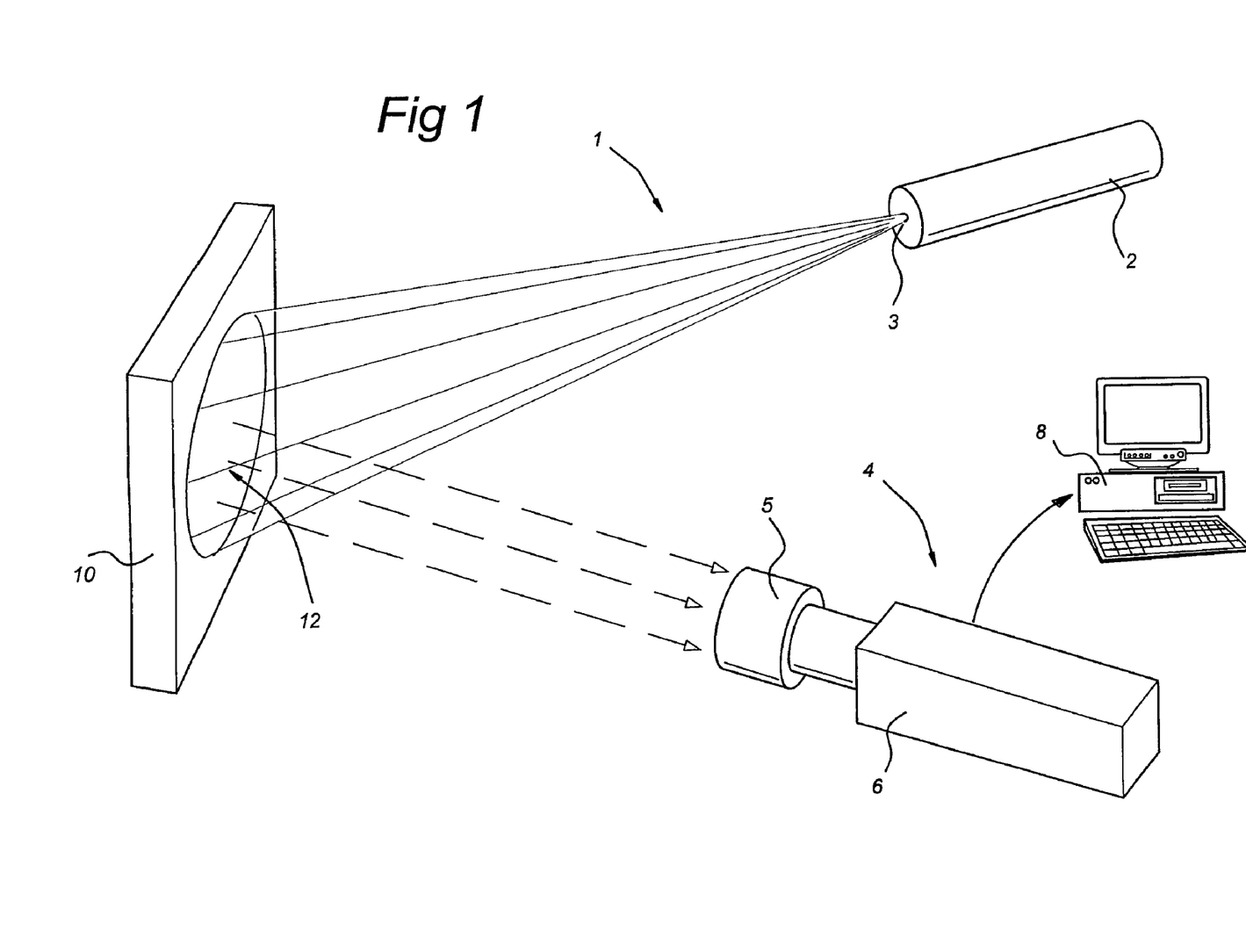
FIG. 1 shows schematically a Laser Doppler Perfusion Imaging system according to the present invention.

FIG. 1 shows schematically a Laser Doppler Perfusion Imaging system according to the present invention.

A Laser Doppler Perfusion Imaging system 1 comprises a laser light source 2 and a image detection system 4. The beam of the laser light source 2 is aimed at a sample 10. On the sample 10 a surface area of interest 12 is selected where the system 1 will collect Laser Doppler Perfusion data. The image detection system 4 comprises a CMOS image sensor 6 as detector for collecting images of reflected (and possibly Doppler modified) laser light from the selected area of interest 12 on the sample 10. The image detection system uses imaging means (i.e. a lens system 5) for imaging the surface of the sample 10 on the CMOS image sensor 6 to collect an image comprising Laser Doppler signals for each detector element within the CMOS image sensor 6.

The image detection system 4 is connected to a computer arrangement 8 for downloading a collected image to the computer 8. The computer 8 is arranged to gather and extract relevant Laser Doppler Perfusion data from the collected image, as will be explained below in more detail.

The laser light source 2 may use laser light of any suitable wavelength and any usable output power, preferably in the visible part of the spectrum.

For example, a He—Ne laser with a wavelength of 632.8 nm and an output power of 10 mW is used. Other wavelengths may be used as well. Also, it is conceivable to use a pulsed laser instead of a continuous laser.

Further, the laser light source 2 comprises beam shaper 3 for shaping the laser beam to illuminate the area of interest 12 on the sample 10. Here, the beam shaper 3 can provide various profiles e.g. uniform, dot matrix, line, or a beam profile comprising a plurality of beams arranged in a (dot) matrix form, a rectangular array of beams, or any other conceivable pattern of beams, etc. Here, only two beam profiles are considered, although other shapes may be used as well:

Gaussian beam profile: the diameter of the uniform part of the laser spot at the area of interest 12 on the sample surface 10 is used to obtain an expanded output beam from the laser source by using simple optics such as a beam expander (not shown).

Dotted beam profile: a plurality of laser spots placed around the central one. This pattern is obtained from the output beam of the laser light source 2 by using a beam splitter. Such a beam splitter may be a diffractive beamsplitter and is available from Thorlabs Inc., (G1030A). This type of illumination advantageously increases the signal-to-noise ratio of the Laser Doppler Perfusion system 1 since the laser power is concentrated in a plurality of points of interest and not smeared in a single wide spot.

The sample surface 10 is imaged through an objective lens 5 on the CMOS image sensor 6. The CMOS image sensor used here as example is a FUGA 15D from Fillfactory, Belgium, and comprises 512×512 pixels with a pixel-size of 12×12 µm².

Besides the more general features mentioned above for CMOS sensors, the FUGA 15D has some more specific features:

High dynamic range, about 120 dB, or 6 light decades. This high dynamic range is a result of the logarithmic conversion from light energy to a voltage level in the pixels, CCDs and many CMOS sensors from the prior art have a linear conversion from light to voltage, which means that the disc range is much lower, often between 60 and 70 dB. This will result in a saturation of under-sensitivity of the detector from the prior art, as described above.

No blooming. The CMOS image sensor pixels are non-integrating, after being activated they measure throughput, not volume. A saturated pixel will never overflow and influence a neighbouring pixel. Such anti-blooming feature in combination with the high dynamic range makes the CMOS image sensor very well suited for imaging scenes with a high dynamic illumination range, such as laser spots.

Typically, in the Laser Doppler Perfusion Imaging system the distance between the image detection system 4 and the sample 10 is about 5-100 cm.

It is noted here that by using a CMOS image sensor 6 both the area of interest 12 on the surface 10 and the Doppler signal are imaged with a single detector. In this manner, the co-ordination between the visible image of the sample and the Doppler signals is well defined. Advantageously, the position of a received Doppler signal can easily be determined within the visible image.

Further, the Laser Doppler Perfusion Imaging system of the present invention allows depth-resolved laser Doppler imaging. By measurement of a laser Doppler signal on detector elements of the CMOS image sensor as a function of the lateral distance of an incoming laser beam focussed on the sample, information on perfusion as a function of depth can be obtained as well. At larger lateral distance between detector element position and the image of the incoming beam (source), the detected photons (which diffusively scattered in the sample) have a larger average penetration depth than those photons detected at a close distance to the source. Therefore, blood flow in surface layers can be distinguished from blood flow in deeper regions of the sample. The depth-resolved measurement will be explained in more detail with reference to FIGS. 7A and 7B.

Figure 2:
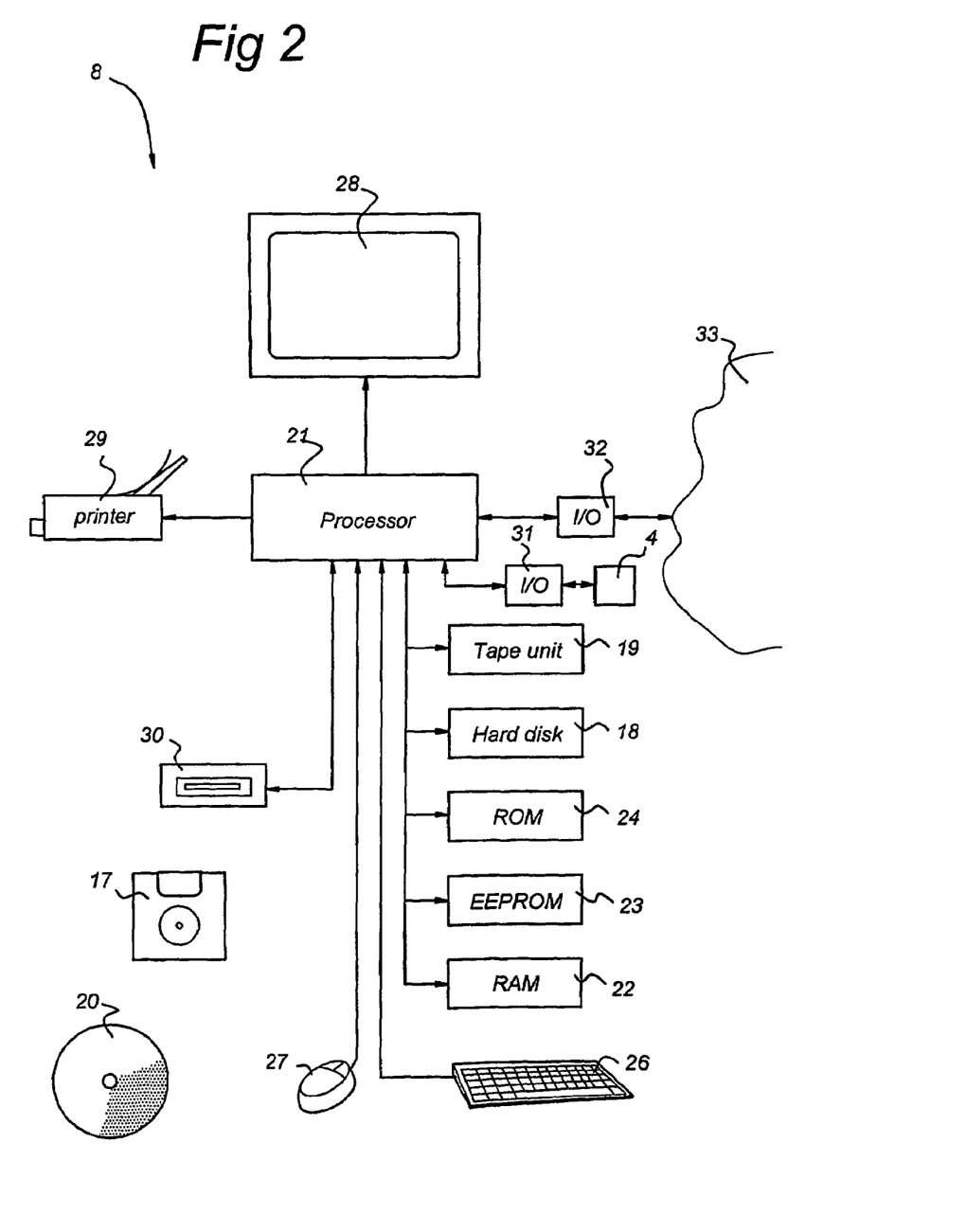
FIG. 2 shows schematically a computer arrangement as used in the system according to the present invention.

FIG. 2 shows schematically a computer arrangement 8 as used in the system according to the present invention.

Computer arrangement 8 comprises host processor 21 with peripherals. The host processor 21 is connected to memory units 18, 19, 22, 23, 24 which store instructions and data, one or more reading units 30 (to read, e.g., floppy disks 17, CD ROM's 20, DVD's, etc.), a keyboard 26 and a mouse 27 as input devices, and as output devices, a monitor 28 and a printer 29. Other input devices, like a trackball, a touch screen or a scanner, as well as other output devices may be provided.

An input/output (I/O) device 31 is provided for a connection to the image detection system 4. The I/O device 31 is arranged for image-related data-transmission from the image detection system 4.

Further, a network I/O device 32 is provided for a connection to a network 33.

The memory units shown comprise RAM 22, (E)EPROM 23, ROM 24, tape unit 19, and hard disk 18. However, it should be understood that there may be provided more and/or other memory units known to persons skilled in the art. Moreover, one or more of them may be physically located remote from the processor 21, if required.

The processor 21 is shown as one box, however, it may comprise several processing units functioning in parallel or controlled by one main processor, that may be located remotely from one another, as is known to persons skilled in the art.

The computer arrangement 8 of the present invention is capable of receiving images which are captured by the image detection system 4 and consecutively transmitted. The processor 21 are capable to perform calculations on an image on a pixel-by-pixel basis and to extract Laser Doppler Perfusion data from these received (and processed) image data.

Figure 3:
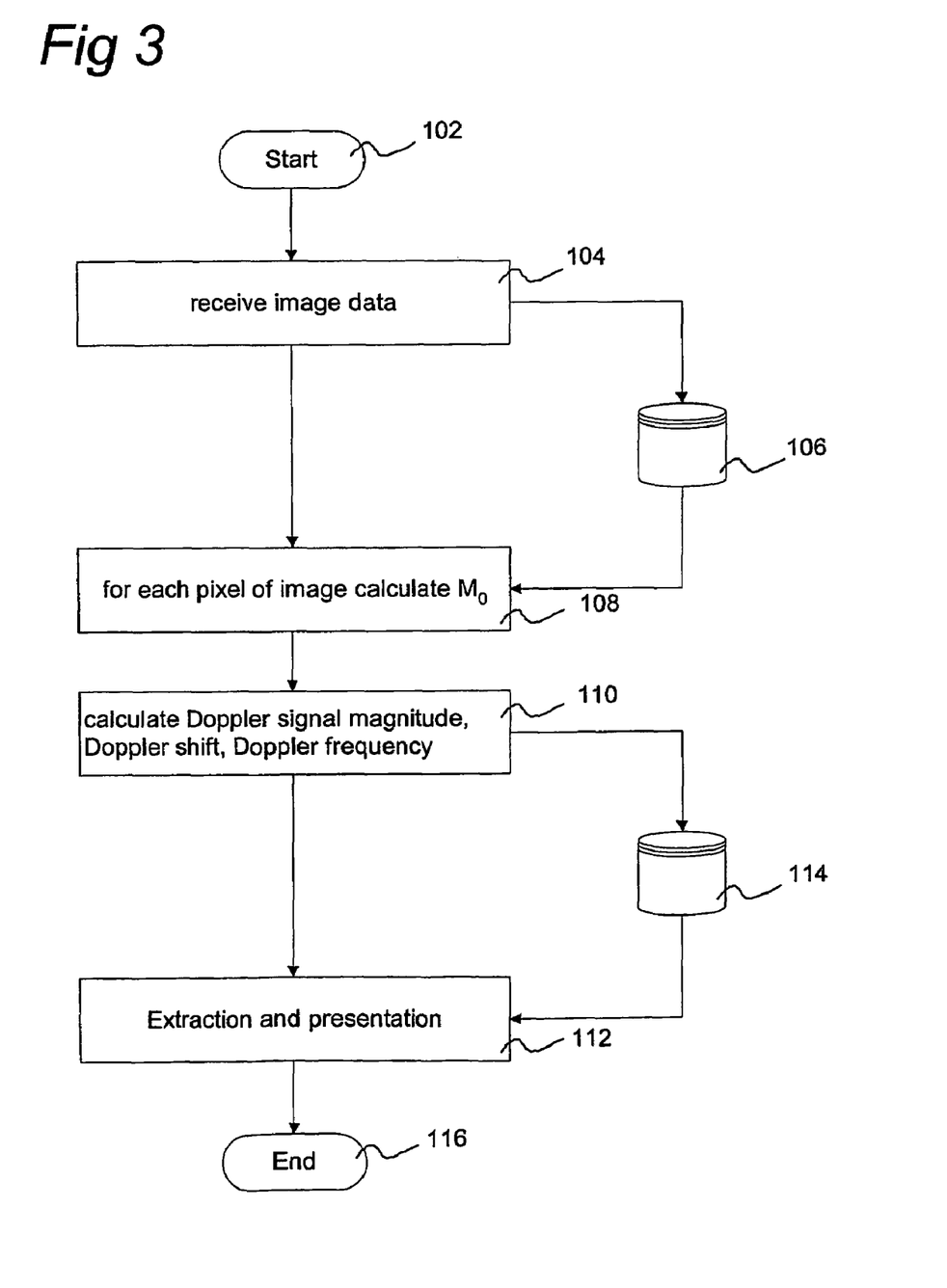
FIG. 3 shows a block diagram for a procedure to be carried out by the computer arrangement in order to perform Laser Doppler Perfusion Imaging in a Laser Doppler Perfusion Imaging system according to the present invention.

FIG. 3 shows a block diagram for a procedure 100 to be carried out by the computer arrangement in order to perform Laser Doppler Perfusion Imaging in a Laser Doppler Perfusion imaging system according to the present invention.

The procedure 100 starts at the entry point 102.

In step 104, the image data are collected (scanned) in an imaging procedure. The imaging procedure is as follows. In full-frame mode (as an example 512×512 pixels) an area of interest 12 on the sample surface 10 is defined with a size of e.g., 64×64 pixels, Thus, the co-ordinates of each pixel are related to a location within the image of the area of interest 12. Then N frames of the area of interest 12 are scanned.

It is noted that CMOS image array 6 has a X-Y co-ordinate readout determined by the array architecture. This readout facilitates windowed readouts, which provide for electronic zoom functions. Readout can be also performed by skipping lines or columns that only reduces the image resolution: e.g., even full frame (e.g., 512×512 pixels) can be zoomed to 64×64 pixels by readout only each 8$^{th}$ line and column from the full frame—1, 8, 16, . . . , 512.

It is noted that inage sensors with other pixel numbers may be used as well: manipulation of e.g., the image resolution, can be done similarly as described above.

Further, it is noted that pixels from the 64×64 frame are read out consecutively: first, pixels of the upper line are sampled sequentially one by one from the rows. Fast sampling rate allows all pixels from the line to be read out at almost the same instant (thus, the time constant of the Doppler signal is larger than the time constant of the acquisition system). The delay between the readout of the first and the last pixel is about 1 μs. After collecting N samples for each pixel from the line, the next line is being readout.

The collected image data 106 are stored in memory means 18, 19, 22, 23, 24.

In step 108, signal processing is performed on the collected image data stored in 106.

The signal processing comprises calculation of the modulation depth $V_{i,j}$ of the intensity fluctuations for each pixel $$V_{i,j} = \langle (I_{i,j} - \langle I_{i,j}\rangle)^2 \rangle / \langle I_{i,j}\rangle_N^2, \ i,j = 1.64. \quad (1)$$

where $I_{i,j}$ and $\langle I_{i,j}\rangle$ are the instantaneous and average intensity at the i,j$^{th}$ pixel, respectively. $\langle I_{i,j}\rangle_N$ is the intensity of i,j$^{th}$ pixel, averaged over N images The quantity $V_{i,j}$ is equivalent to the normalised zeroth moment of the photo-current power spectrum P(ω). Normalization is obtained through dividing P(ω) by $\langle I_{i,j}\rangle^2$.

$$M_0 = \int P(\omega) / \langle I_{i,j}\rangle^2 \, d\omega, \quad (2)$$

where ω is the Doppler frequency.

As known by persons skilled in the art, other normalisation factors may be used (e.g., $\langle I_{i,j}\rangle$).

$M_0$ relates to the concentration of moving particles in the sampling volume.

In a next step 110 the processor 21 defines for each pixel, the Doppler signal magnitude $M_0$, and the average Doppler shift $M_1/M_0$. $M_1$ represents the first moment of the photo-current power spectrum P(ω) and relates to the speed of moving particles in the sampling volume.

As known to persons skilled in the art, higher order moments (e.g., $M_2$) of photo-current power spectrum P(ω) may be used as well.

Since for each pixel N samples have been collected, the measured signal for each pixel can be analysed as a function of time. It is noted that on present generation computer systems processor 21 may use such a clock speed that the signal may be measured in (almost) real-time.

The calculated data are preferably stored as data-maps 114 in the memory means 18, 19, 22, 23, 24.

In stop 112, the processor 21 carries out a procedure for the extraction of Doppler-related data from the data maps 114. Typically, such a procedure may comprise some interaction with a user of the system by means of a query procedure as known in the art.

The results may be presented in various ways, e.g., the results may be displayed as an image in 2-D grayscale (e.g., 256 shades at 8-bit resolution) or false-colour (e.g., 256 colors at 8-bit resolution) coded maps, describing the spatial variation of the moving particle concentration in the examined area of interest 12.

The procedure 100 ends in step 116.

FIGS. 4A, 4B, 4C and 4D show an example of an in-vitro Laser Doppler Perfusion Imaging experiment.

Figure 4A:
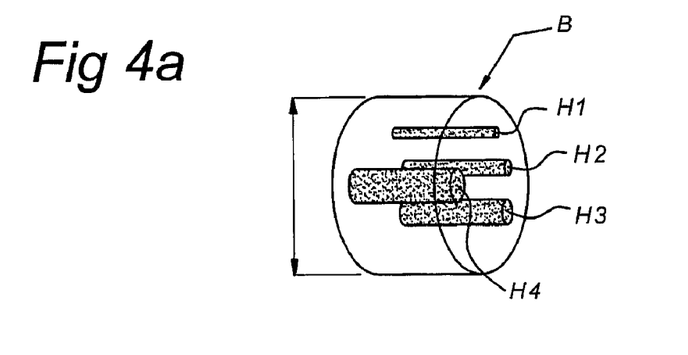
FIGS. 4A, 4B, 4C, and 4D show an example of an in-vitro Laser Doppler Perfusion Imaging experiment.

In FIG. 4A, a schematic drawing is shown of an artificial object comprising a circular white plastic (Delrin) block B with four holes H1-H4 of different diameter perpendicular to the side illuminated by the laser light source 2. The holes H1-H4 were filled with a water suspension of 10% Intralipid™ at 10% concentration and then closed with scotch tape of 50 μm thick to avoid liquid leakage.

Figure 4B:
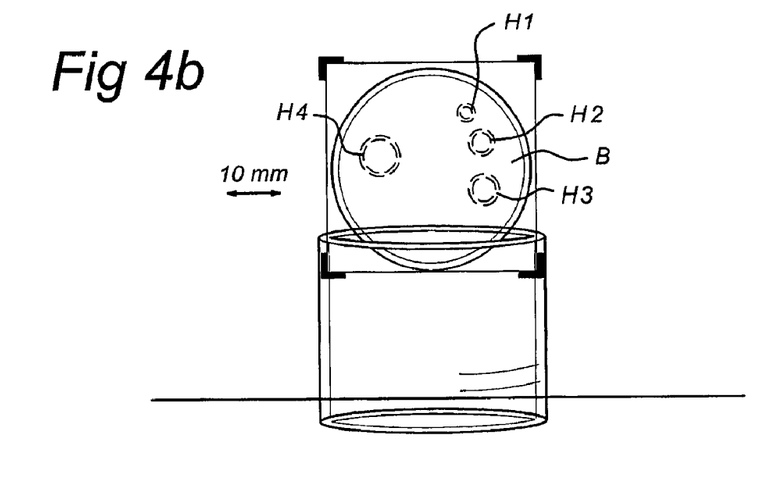
Figure 4C:
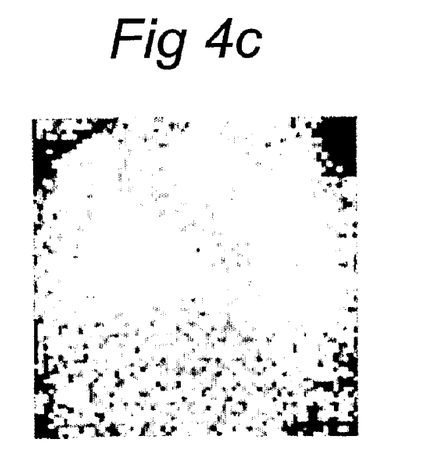
Figure 4D:
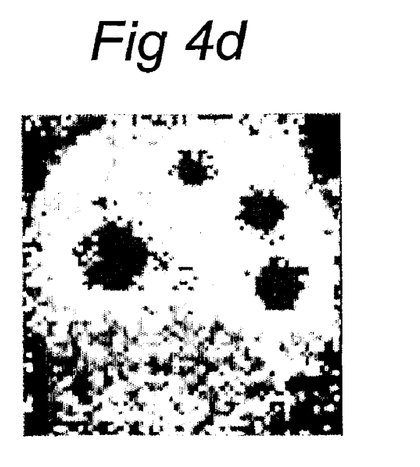

FIGS. 4B, 4C and 4D show the photographic image of a sample (FIG. 4B) (full frame; 512×512 pixels) and corresponding gray-scale (FIG. 4C) and false-colour (FIG. 4D) moving particles concentration maps (192×192 pixels stretched from 64×64 imaged pixels) respectively, as obtained with the image detection system 4 equipped with CMOS image sensor 6. Lighter areas on the gray-shadow flow maps indicate regions with a higher concentration of moving particles. The dashed lines on the sample image (FIG. 4B) mark the location of the flow areas.

Results obtained from this sample clearly demonstrate the dynamic range of the imaging system 4 since the sample contains both purely statically and dynamically scattering regions which are well resolved an the data map images.

FIGS. 5A, 5B, 5C, 5D and 5E show an example of an in-vivo Laser Doppler Perfusion Imaging experiment.

Figure 5A:
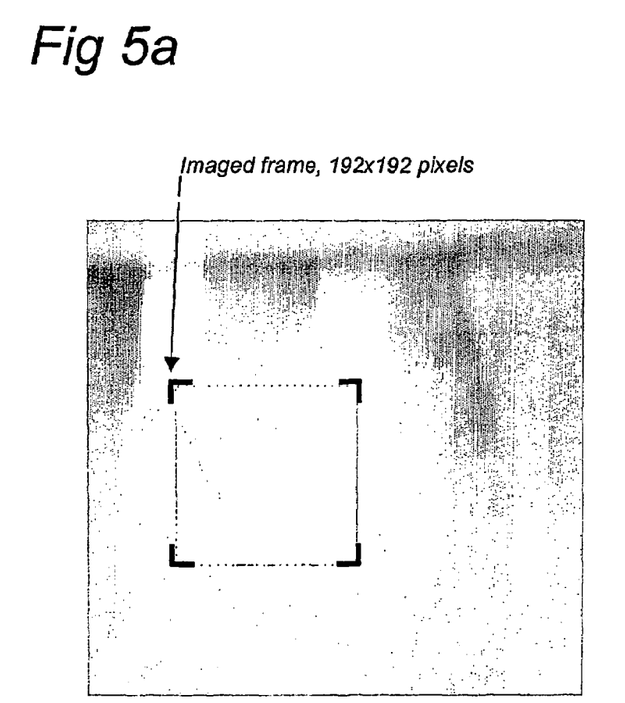
FIGS. 5A, 5B, 5C, 5D and 5E show an example of an in-vivo Laser Doppler Perfusion Imaging experiment.

FIG. 5A shows the photographic image of a sample, a finger tip, in full frame: 512×512 pixels.

Figure 5B:
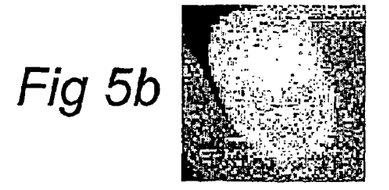
Figure 5C:
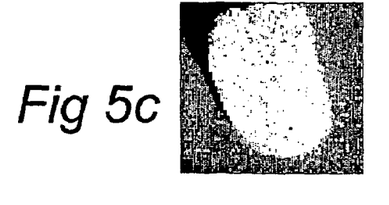

FIGS. 5B and 5C show the corresponding gray-scale moving particles concentration maps (192×192 pixels stretched from 64×64 imaged pixels) before and during occlusion, respectively, as obtained with the the image detection system 4 equipped with CMOS image sensor 6.

Figure 5D:
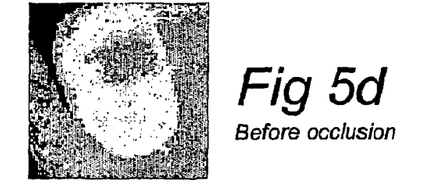
Figure 5E:
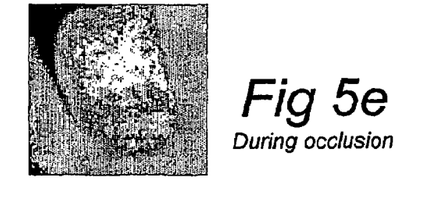

FIGS. 5D and 5E show the corresponding false-colour moving particles concentration maps (192×192 pixels stretched from 64×64 imaged pixels) before and during occlusion, respectively, as obtained with the image detection system 4 equipped with CMOS image sensor 6.

Perfused areas on the finger are clearly seen on the flow maps (FIGS. 5B and 5D) before the occlusion of the upper arm. The flow maps (FIGS. 5C and 5E) obtained during the occlusion show an obvious decrease of the concentration of moving blood cells. During the occlusion, most of the blood cells in the occluded part stop their movement. This results in a decrease of the fraction of Doppler-shifted photons in the scattered laser light that is responsible for the strength of the intensity fluctuations on the CMOS image sensor 6.

Figure 6A:
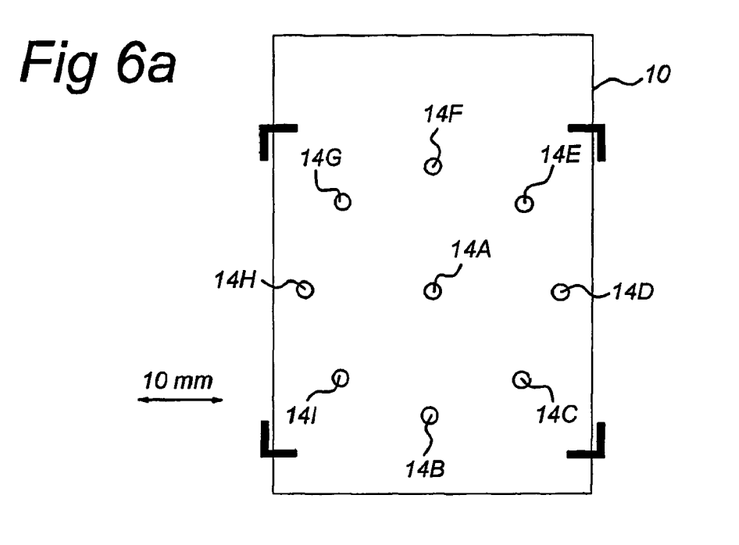
FIG. 6 shows an example of an in-vitro Laser Doppler Perfusion Imaging experiment by using a beam profile comprising a plurality of laser beams generated by the optical means of the Laser Doppler Perfusion Imaging system according to the present invention.
Figure 6B:
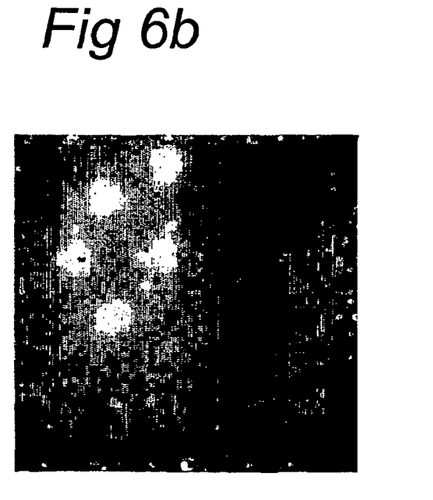
Figure 6C:
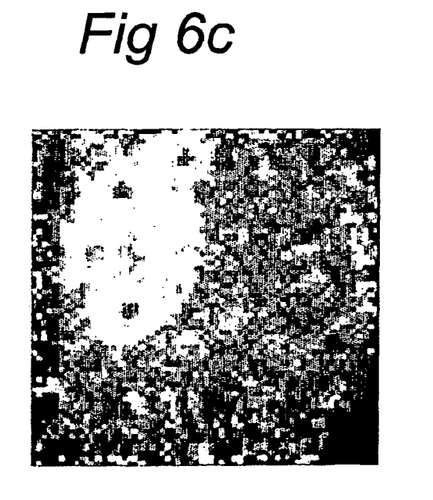

FIGS. 6A, 6B, 6C show an example of an in-vitro Laser Doppler Perfusion Imaging experiment by using a beam profile comprising a plurality of laser beams generated by the optical means of the Laser Doppler Perfusion Imaging system according to the present invention.

FIG. 6, a beam profile comprising a plurality of laser beams as generated by the optical means 3 of the Laser Doppler Perfusion Imaging System 1 is used for illuminating of a sampling area 10.

Optical means 3 comprise for example a diffractive grating for generating a plurality of laser beams as shown. The optical means 3 of the laser Doppler Perfusion Imaging System 1 act as beamsplitter and generate multiple laser beams which impinge on the surface of sample 10. The plurality of laser beams impinging on the sample 10 are depicted by open circles 14A, 14B, 14C, 14D, 14E, 14F, 14G, 14H, 14I.

By using such a set-up with an optical means 3 to split the incoming beam from laser 2 in a plurality of laser beams, the energy of the incoming beam from laser 2 is substantially conserved, and, hence, a substantially higher intensity of each of the plurality of beams is available for measurement of the Doppler effect. By measurement of a plurality of beams a higher signal-to-noise ratio is obtained than for a single laser beam.

FIG. 6B shows the corresponding gray-scale moving particles concentration map (192 by 192 pixels stretched from 64 by 64-imaged pixels). FIG. 6C shows the corresponding false-color moving particles concentration map.

Figure 7A:
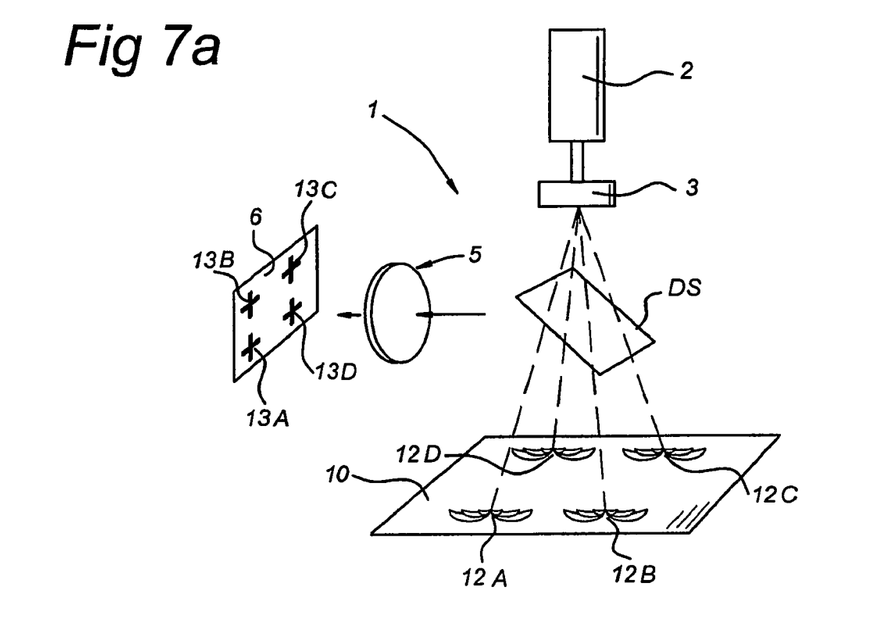
FIGS. 7A and 7B show schematically the principle of depth-resolved Laser Doppler Perfusion Imaging in accordance with the Laser Doppler Perfusion Imaging system of the present invention.
Figure 7B:
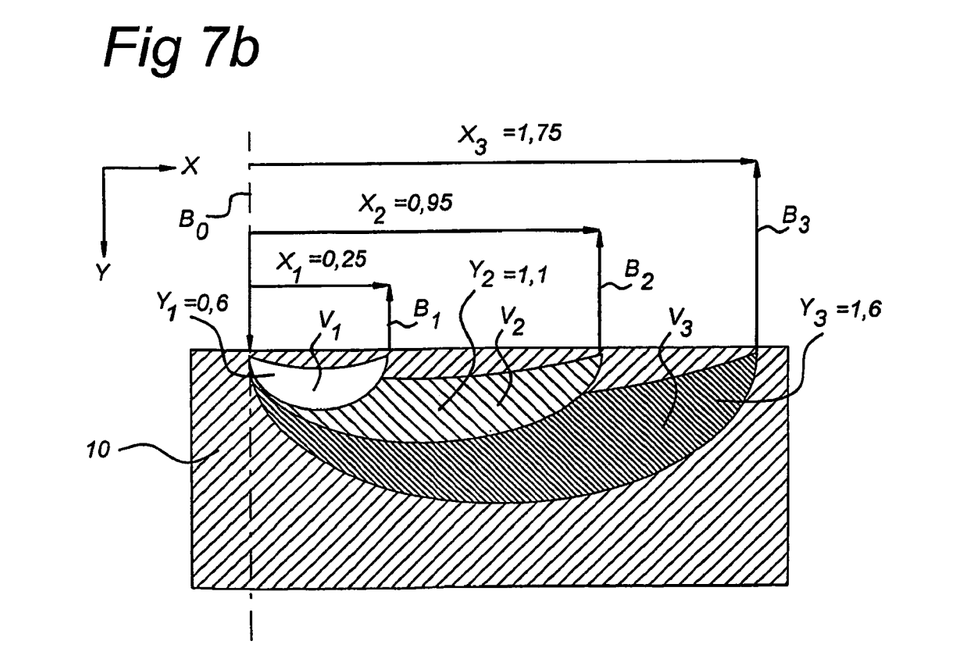

FIGS. 7A and 7B show schematically the principle of depth-resolved Laser Doppler Perfusion Imaging in accordance with the laser Doppler Perfusion Imaging System of the present invention. In FIGS. 7A and 7B, entities with the same reference number as used in the preceding figures, refer to the same entities.

In FIG. 7A, an embodiment of the laser Doppler Perfusion Imaging System according to the present invention is shown. The optical means 3 of the laser Doppler Perfusion Imaging System 1 acts as beamsplitter and generates multiple laser beams which, after passing through a semi-transparent mirror DS, impinge on the surface of sample 10.

In the areas of interest 12A, 12B, 12C, 12D, illuminated by the plurality of laser beams, incoming photons from the respective laser beams are scattered in the volume under the respective areas. The scattered photons that depart from the surface 10, are reflected by the semi-transparent mirror DS and, subsequently, imaged on the CMOS image sensor 6 by the imaging means 5.

The crosses 13A, 13B, 13C, 13D indicate the active pixel patterns on the CMOS image sensor 6 for the respective areas 12A, 12B, 12C, 12D. Thus, various areas of interest may be measured simultaneously in the embodiment as shown here.

In FIG. 7B the principle of depth sensitive imaging is further explained. Depth sensitive imaging can be accomplished by using various illumination-to-detection distances for a given incoming laser beam and photons from that beam that are scattered in the sample.

The incoming beam B0 impinges on the surface of sample 10. In the volume of the sample 10 tree volumes V1, V2, V3 are shown. Here, as an example, three volumes are shown for three distinct average probe depths. Persons skilled in the art will recognize that more and/or other volumes and corresponding average probe depths may be chosen.

The volumes represent the envelope for a given average probe depth as a function of the distance of the photon escape position relative to the incoming beam B0. The photon escape position is schematically shown by the arrows B1, B2, B3. The distance of the respective photon escape position relative to the impinging beam B0 is given by the horizontal arrows X1, X2, X3.

For a relatively short horizontal distance X from the impinging beam B0 the average probe depth is small. For large distances from the impinges beam $b_0$ the average probe depth will be larger since the longer horizontal distance form the incoming beam B0 allows for a relatively longer scattering length of photons within the sample.

In FIG. 7B, as an example, the scattering in a sample is illustrated.

It is noted that here the scattering volumes V1, V2, V3 have an axis of rotational symmetry coinciding with incoming beam B0, perpendicular to the surface. For a radial distance of X1=0.25 mm, the photons escaping at position B1 comprise an average probe depth of 0.6 mm. For a radial distance X2=0.95 mm, the photons escaping at photon escape position B2 have experienced an average probed depth of 1.1 mm. For a radial distance X3=1.75 mm, the photons escaping at photon escape position B3 have experienced an average probe depth of 1.6 mm.

It is noted that for oblique incidence of the incoming beam B0, the relation between average probe depth and photon escape position and the spatial distribution of the scattering volumes may be different.

With the Laser Doppler Perfusion Imaging system according to the present invention, the combination of photographic imaging of a sample and measurement of a Doppler signal in that sample with use of a single sensor allows for an easy and precise superposition of the flow map on the area of interest 12 on the surface 10 of the sample. This is particularly important in situations where the perfusion image must be correlated with the visual appearance of the skin, for instance in skin ulcers and in burns.

Since one single 2-D CMOS image sensor 6 is utilised for Doppler measurements as well as for observing the object of interest, now it is easy to align the focusing optics properly to find the area of interest 12 in the 2-D array field of view. Also this approach simplifies use of powerful zooming optics for imaging without loosing the object from the CMOS image sensor view field. It enables an opportunity for Doppler imaging from a distance of several meters or more if required.

By using a CMOS image sensor 6 in the Laser Doppler Perfusion Imaging system 1 according to the present invention, the measurement accuracy is improved since no mechanical motion is involved. Also, absence of moving components for scanning increases the scanning speed of the system, and decreases artefacts caused by movement of the laser beam.

The Laser Doppler Perfusion Imaging system 1 has an extended dynamic range for particle flow speed since no integration time is involved: the photo-current in the CMOS image sensor 6 is continuously converted in a output voltage without integration of the signal during the sampling time interval.

Due to the high dynamic intensity range of the CMOS image sensor 6, the Laser Doppler Perfusion Imaging system 1 is capable of measurements on highly reflective surfaces without saturation of the photo sensors in the CMOS image sensor 6. This sensor property has a further advantage that the object of interest can be observed even when being illuminated by a laser beam. It allows for easier finding of the illuminated object in the camera view field and/or aligning of the laser beam on the area to be illuminated during direct observation in the camera. Also, the system is less sensitive to background illumination (e.g., daylight).

Further, CMOS technology provides the ability to integrate digital signal processing (DSP) functions on the CMOS image sensor chip: i.e., sensor-control logic, DSP and microprocessor cores, and internal memory.

DSP functions add a fully programmable processing feature to the CMOS image sensor. Such tasks as noise filtering, compression, output-protocol formatting, electronic-shutter control, and sensor-array control may be performed by the DSP and enhance the performance of the CMOS image sensor device within a Laser Doppler Perfusion Imaging system.

Thus, in further embodiment of the Laser Doppler Perfusion Imaging system 1 according to the present invention, the CMOS image sensor 6 is adapted for full-frame laser Doppler imaging for simultaneously reading out the photo detector signals and performing DSP functions such as a Fast Fourier Transform (FFT).

Because of such integration of image capturing and signal processing, products such as low-power cameras on a chip are possible, e.g. a wireless camera for monitoring of blood flow, including catheter applications.

It is noted that such DSP functions may also be executed by a digital signal processor located remotely from the imager 6 (or by a (general purpose) microprocessor, a logical circuit, or any other means capable of processing the data from the imager as known to persons skilled in the art).

In yet another embodiment, covering a CMOS image sensor 6 with an RGB mask (such sensors already exist for colour imaging) yields the possibility to perform Laser Doppler Perfusion Imaging at three different wavelengths simultaneously, although at the expense of image resolution. Thus, depth discriminative measurements of blood flow are possible since different wavelengths have different sampling depth depending on the light scattering and absorption properties of the sample under investigation.

Although here the present invention is described by an exemplary CMOS image sensor, it will be appreciated that any type of a two-dimensional random access high pixel readout rate image sensor may be applied.

The invention claimed is:

1. Laser Doppler Perfusion Imaging system comprising a laser light source, an image detector, and signal detector; said laser light source, in use, being arranged for illuminating a selected area of interest on a sample for determining perfusion-related data of said sample, said image detector, in use, being arranged for capturing an image of said sample, and said signal detector, in use, being arranged for detecting a laser Doppler signal from said selected area of interest on said sample, wherein said laser light source comprises optical means for creating a laser beam comprising a plurality of beams, the optical means acting as a beam splitter and generating multiple laser beams impinging on the sample, for simultaneous measurement of various areas of interest.

2. The Laser Doppler Perfusion Imaging system according to claim 1 wherein said perfusion-related data comprise depth-resolved perfusion-related data.

3. The Laser Doppler Perfusion Imaging system according to claim 1, wherein said image sensor comprises on-chip signal processor (DSP) for pre-processing of said laser Doppler signal from said selected area of interest on said sample for each detector element of said image sensor.

4. The Laser Doppler Perfusion Imaging system according to claim 1, wherein said pre-processing of said laser Doppler signal by said on-chip signal processor (DSP) of said image sensor comprises the following processing steps: noise filtering, compression, and time and frequency domain related calculation of said laser Doppler signal.

5. The Laser Doppler Perfusion Imaging system according to claim 1, wherein said pre-processing of said laser Doppler signal by said on-chip signal processor (DSP) of said image sensor comprises the following image sensor controlling steps: output-protocol formatting, electronic-shutter control, sensor-array control.

6. The Laser Doppler Perfusion Imaging system according to claim 1, wherein said image sensor comprises a wavelength discriminating mask, such as an RGB mask.

7. Method to be performed by a signal processor arranged for use in a Laser Doppler Perfusion Imaging system according claim 1, said signal processor comprising processor, memory means, and input/output means, said processor being connected to said memory means and to said input/output means, said input/output means being connected to said image detector, wherein said processor is arranged to carry out the following step: to determine said perfusion-related data from said laser Doppler signal from said selected area of interest on said sample for each detector element in said image sensor.

8. A combination comprising a computer program on a computer readable medium, adapted for loading on a signal processor and a Laser Doppler Perfusion Imaging system according to claim 1, said signal processor comprising a processor , memory means, and input/output means , said processor being connected to said memory means and to said input/output means, said input/output means being connected to said image detector of said Laser Doppler Perfusion Imaging system , wherein said computer program when loaded is configured to allow said signal processor to carry out the following step: determining said perfusion-related data from said laser Doppler signal from said selected area of interest on said sample for each detector element in said image sensor.

9. The Laser Doppler Perfusion Imaging system comprising a laser light source, an image detector, and signal detector; said laser light source, in use, being arranged for illuminating a selected area of interest on a sample for determining perfusion -related data of said sample, said image detector, in use, being arranged for capturing an image of said sample, and said signal detector, in use, being arranged for detecting a laser Doppler signal from said selected area of interest on said sample, wherein said image detector embodies said signal detector, said image detector being a two-dimensional random access high pixel readout rate image sensor device, the area of interest and the Doppler Signai being imaged with the single signal detector.

10. The Laser Doppler Perfusion Imaging system according to claim 9, wherein two-dimensional random access high pixel readout rate image sensor comprises a CMOS image sensor device.

11. The Laser Doppler Perfusion Imaging system according to claim 10, wherein said image detector is arranged for connecting to a signal processor, said signal processor comprising processor, memory means, and input/output means, said processor being connected to said memory means and to said input/output means, said input/output means being connected to said image detector; said processor being arranged to carry out the following step: to determine said perfusion-related data from said laser Doppler signal from said selected area of interest on said sample for each detector element in said image sensor.

12. The Laser Doppler Perfusion Imaging system according to claim 10, wherein said perfusion-related data comprise at least Doppler magnitude (Mo), and average Doppler shift ($M_1$) of said laser Doppler signal.

13. The Laser Doppler Perfusion Imaging system according to claim 9, wherein said image detector is arranged for connecting to a signal processor, said signal processor comprising processor, memory means, and input/output means, said processor being connected to said memory means and to said input/output means, said input/output means being connected to said image detector; said processor being arranged to carry out the following step: to determine said perfusion-related data from said laser Doppler signal from said selected area of interest on said sample for each detector element in said image sensor.

14. The Laser Doppler Perfusion Imaging system according to claim 13, wherein said perfusion-related data comprise at least Doppler magnitude (Mo), and average Doppler shift ($M_1$) of said laser Doppler signal.

15. The Laser Doppler Perfusion Imaging system according to claim 9, wherein said perfusion-related data comprise at least Doppler magnitude (Mo), and average Doppler shift ($M_1$) of said laser Doppler signal.

* * * * *